United States Patent [19]

Beight et al.

[11] Patent Number: 4,595,687
[45] Date of Patent: Jun. 17, 1986

[54] SPARSOMYCIN DERIVATIVES

[75] Inventors: Douglas W. Beight, Cincinnati; Gary A. Flynn, Madeira, both of Ohio

[73] Assignee: Merrell Dow Pharmaceuticals Inc., Cincinnati, Ohio

[21] Appl. No.: 632,133

[22] Filed: Jul. 18, 1984

[51] Int. Cl.$^4$ .............. A61K 31/505; C07D 239/10
[52] U.S. Cl. ................................ 514/274; 544/311; 548/239; 549/479; 560/17; 560/106; 562/557; 564/440
[58] Field of Search ............... 544/309, 311; 424/251; 514/274

[56] References Cited

FOREIGN PATENT DOCUMENTS 0108455  5/1984  European Pat. Off. ............ 544/311

OTHER PUBLICATIONS

Goldberg and Mitsugi, *Biochemical and Biophysical Research Communications*, vol. 23, No. 4, 1966, pp. 453–459.
Lin and Dubois, *J. Med. Chem.*, vol. 20, No. 3, pp. 337–341, (1977).
Burger, A., *Medicinal Chemistry*, 2nd ed. ©1960, p. 42.
Ottenheijm and Liskamp, *Tetrahedron Letters*, No. 27, pp. 2437–2438, 1978 (I).
Ottenheijm, Liskamp and Tijhvis, *Tetrahedron Letters*, No. 4, pp. 387–390, 1979 (II).
Duke, *Dissertation Abstracts International*, vol. 43, No. 10, p. 3249B, Apr. 1983.
Upjohn Co. *Chemical Abstracts*, vol. 62:5855d (1965).
Flynn and Ash *Biochemical and Biophysical Research Communications*, vol. 114, No. 1, 1983, Jul. 18, 1983, pp. 1–7, Necessity of the Sulfoxide Moiety for the Biochemical and Biological Properties of an Analog of Sparsomycin.
Ash et al., Antimicrobial Agents and Chemotherapy, Apr., 1984, pp.–443–445, vol. 25, No. 4, Importance of the Hydrophobic Sulfoxide Substituent on Nontoxic Analogs of Sparsomycin.

*Primary Examiner*—Donald G. Daus
*Assistant Examiner*—Stephen M. Kapner
*Attorney, Agent, or Firm*—Stephen L. Nesbitt

[57] ABSTRACT

Sparsomycin derivatives of the formula

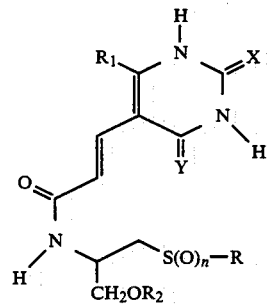

wherein X and Y are each independently an oxo or an imino group; n is 0 or the integer 1 or 2; $R_1$ is a hydrogen or 1 to 4 carbon alkyl group; $R_2$ is a hydrogen, a 1 to 4 carbon alkyl, a 2 to 5 carbon acyl or a benzoyl group; and R is a 1 to 6 carbon alkyl, 3 to 8 carbon alkenyl, cyanomethyl carboxymethyl, carbalkoxymethyl wherein the alkoxy moiety is a 1 to 4 carbon alkoxy group, nitromethyl, alkylcarbonylmethyl wherein the alkyl moiety is a 1 to 4 carbon alkyl group, pyridyl, furanyl, or furfuryl group or a phenyl or benzyl group optionally substituted by a methylenedioxy or one to two halogen, 1 to 4 carbon alkyl, 1 to 4 carbon alkoxy, 1 to 4 carbon alkylthio, hydroxy, nitro or cyano groups or a pharmaceutically acceptable acid addition salt thereof. Also described are their use as antiprotozoals and antibacterials.

8 Claims, No Drawings

SPARSOMYCIN DERIVATIVES

FIELD OF THE INVENTION

This invention relates to certain Sparsomycin derivatives as well as their use as antibacterials and antiprotozoals, in particular antitrypanosomals

DESCRIPTION OF THE PRIOR ART

The Sparsomycin derivatives of this invention are known in the prior art, see R. J. Ash et al. Antimicrobial Agents and Chemotherapy, April 1984 p. 443-445 and G. A. Flynn and R. J. Ash, Biochemical and Biophysical Research Communications, vol. 114, No. 1, 1983, July 18, 1983 p. 1-7.

SUMMARY OF THE INVENTION

This invention relates to pharmaceutically active Sparsomycin derivatives of general Formula I

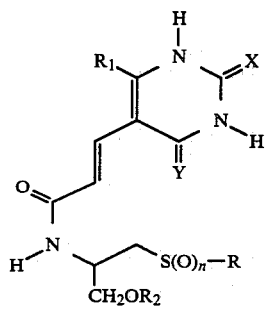

I wherein X and Y are each independently an oxo or an imino group; n is 0 or the integer 1 or 2; $R_1$ is a hydrogen or 1 to 4 carbon alkyl group; $R_2$ is a hydrogen, a 1 to 4 carbon alkyl, a 2 to 5 carbon acyl or a benzoyl group; and R is a 1 to 6 carbon alkyl, 3 to 8 carbon alkenyl, cyanomethyl, carboxymethyl, carbalkoxymethyl wherein the alkoxy moiety is a 1 to 4 carbon alkoxy group, nitromethyl, alkylcarbonylmethyl wherein the alkyl moiety is a 1 to 4 carbon alkyl group, pyridyl, furanyl, or furfuryl group or a phenyl or benzyl group optionally substituted by a methylenedioxy or one to two halogen, 1 to 4 carbon alkyl, 1 to 4 carbon alkoxy, 1 to 4 carbon alkylthio, hydroxy, nitro or cyano groups or a pharmaceutically acceptable acid addition salt thereof. This invention further relates to the use of these Sparsomycin derivatives as antibacterial and antiprotozoal agents.

As used herein, the phrase a 1 to 4 carbon alkyl group includes straight and branched chain alkyl groups such as methyl, ethyl, isopropyl and isobutyl.

As used herein, the phrase a 1 to 6 carbon alkyl group includes straight and branched chain alkyl groups such as methyl, ethyl, propyl, isopropyl, butyl, isobutyl, pentyl, isopentyl, and n-hexyl.

As used herein, the phrase a 1 to 4 carbon atom alkoxy group includes straight and branched chain alkoxy groups such as methoxy, ethoxy, isopropoxy and tert-butoxy.

As used herein, the phrase 1 to 4 carbon atom alkylthio group includes straight and branched chain alkylthio groups such as methylthio, ethylthio, n-butylthio and isobutylthio.

As used herein, the phrase a 2 to 5 carbon atom acyl group includes straight and branched chain acyl groups such as acetyl, propanoyl, butanoyl and isopentanoyl.

As used herein, the phrase a 3 to 8 carbon alkenyl group includes straight and branched chain alkenyl groups wherein the carbon atom at the point of attachment is not an unsaturated carbon atom and includes 2-butenyl, 2-propenyl, 2-methyl-3-ethyl-2-pentenyl, 5-methyl-2-hexenyl and 3-butenyl.

As used herein, the term halogen includes fluoro, chloro, bromo and iodo groups.

As used herein, a cyanomethyl group is taken to mean a group of the formula —$CH_2CN$.

As used herein a carboxymethyl group is taken to mean a group of the formula —$CH_2CO_2H$.

As used herein, a carbalkoxymethyl group is taken to mean a group of the structure

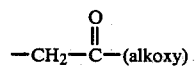

wherein the alkoxy moiety is a 1 to 4 carbon alkoxy group.

As used herein, a nitromethyl group is a group of the formula —$CH_2NO_2$.

As used herein, an alkylcarbonylmethyl group is a group of the structure

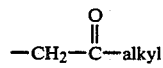

wherein the alkyl moiety is a 1 to 4 carbon alkyl group.

The preferred compounds of this invention are those compounds of Formula I wherein R is a furfuryl or furanyl group or an optionally substituted phenyl or benzyl group. Other preferred compounds are those compounds of Formula I wherein $R_1$ is a methyl group and $R_2$ is a hydrogen group. Yet other preferred compounds are those compounds of Formula I wherein X and Y are oxo groups. Finally, the preferred compounds of this invention include those compounds of Formula I wherein R is a 3 to 8 carbon alkenyl group.

The more preferred compounds of this invention are those compounds of Formula I wherein R is a phenyl or benzyl group optionally substituted at the para position. Also included in the more preferred group of compounds of this invention are those compounds of formula I wherein n is the integer 1.

Especially preferred are those Formula I compounds wherein R is a pyridyl, furanyl or furfuryl group or an optionally substituted phenyl or benzyl group and n is the integer 1 wherein the absolute configuration of the carbon atom bearing the $CH_2OR_2$ group is S and wherein the absolute configuration at the sulfur atom is R. Also preferred are those Formula I compounds wherein R is other than a pyridyl, furanyl or furfuryl group or an optionally substituted phenyl or benzyl group which possess the same relative configuration at the sulfur atom, but which may be designated as R or S depending upon the exact nature of the sulfur atom substituents.

The pharmaceutically acceptable acid addition salts of the compounds of Formula (1) above include the nontoxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the caraboxylic acid in a polar solvent with a stoichiometric quantity of base. In general, the pharmaceutically acceptable salts are crystalline materials which are more soluble in water and various hydrophilic solvents and which in comparison to their free acid forms generally demonstrate higher melting points and an increased chemical stability.

The compounds of this invention can be prepared in any suitable manner by analogous procedures readily known to those skilled in the art. In particular, applicants have prepared the Structure I compounds utilizing one of several synthetic pathways. Although most of the Structure I compounds can be prepared by any of the pathways, due to potential side reactions and unavailability of reactants, one pathway may be preferred over the other for a given desired product as will be readily apparent to the ordinary artisan.

In method A a salt of Structure II is first treated with a base such as triethylamine to yield the corresponding free base.

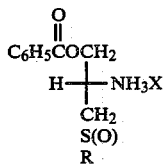

wherein R is as defined above in Structure I and X is an anion, typically chloride ion.

Subsequently, the free amine is coupled with a uracylacrylic acid of Structure III

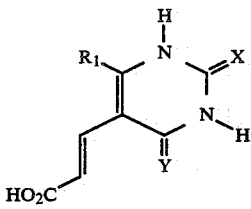

wherein X, Y and $R_1$ are as defined above. Finally base hydrolysis of the benzoyl ester with, for example lithium hydroxide, yields a Structure I compound wherein n is the integer 1 and $R_2$ is a hydrogen group.

In method B a hydroxymethyl compound of Structure IV

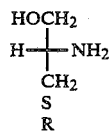

wherein R is as defined above is coupled with a uracylacrylic acid of Structure III to yield a sparsomycin derivative of Structure I wherein $R_2$ is a hydrogen group and n is zero.

In method C an amino ester of Structure V wherein R is as defined above and $R^1$ is a 1 to 4 carbon alkyl group is coupled with a Structure III uracylacrylic acid.

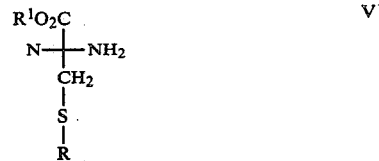

Reduction of the ester group in the resulting coupled product yields a Structure I sparsomycin derivative wherein $R_2$ is a hydrogen group and n is zero.

This ester reduction can be accomplished in any manner generally known in the art which will not affect the other functionalities of the compound. Suitable means of reducing the ester group include metal hydride reductions such as by using lithium aluminum hydride or sodium or lithium borohydride; catalytic reductions employing hydrogen gas and a matallic catalyst such as Raney nickel, platinum, palladium, rhodium, ruthenium and platinum oxide; and dissolving metal reductions employing lithium, sodium, potassium, calcium, zinc, magnesium, tin or iron in liquid ammonia or a low-molecular weight aliphatic amine or sodium, aluminum or zinc amalgam, zinc, tin or iron in a hydroxylic solvent or in the presence of an aqueous mineral or organic acid such as formic, acetic or hydrochloric acid.

As is apparent, the coupling reactions in methods A, B and C are simple amidation reactions and are facilitated by the various reagents known to those skilled in the art such as dicyclohexylcarbodiimide (DCC), N,N'-carbonylodiimidazole, N-ethoxycarbonyl-2-ethoxy-1,2-dihydroquinoline (EEDQ) and diethylcyanophosphonate. Applicants have employed DCC in these coupling reactions preferably in conjunction with a compound such as hydroxybenzotriazole (HOBT) or N-hydroxysuccinimide which is known to increase yields and decrease racemization in DCC facilitated peptide couplings. The couplings are performed by reacting approximately equimolar amounts of an appropriate amine of Structure II, IV or V with a uracylacrylic acid of Structure III for about 1 to 4 days depending on the reactants, the solvent and the temperature which can be from $-20°$ C. to $60°$ C. preferably about $0°$ C. to $25°$ C. or room temperature. A suitable solvent is any nonreactive solvent in which the reactants and coupled sparsomycin product are soluble. Because the solubility of the coupled products is exceedingly low in most organic solvents, the use of dimethylformamide (DMF) is preferred.

The Structure II salt of method A is prepared by acid hydrolysis of an oxazoline sulfoxide of Structure VI

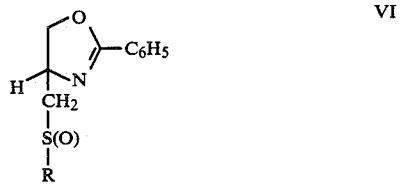

wherein R is as defined above. This hydrolysis is typically performed by allowing the sulfoxide to react in a solution of dilute hydrochloric acid at room temperature. The Structure VI sulfoxide is prepared from the corresponding sulfide by well known oxidation procedures such as by treatment with meta-chloro-peroxybenzoic acid (MCPBA) or 30% hydrogen peroxide solution. The sulfide is in turn prepared by the reaction of a thiol, RSH wherein R is as defined above, with 2-pheny-4-hydroxymethyloxazoline or preferably a more reactive derivative of the hydroxymethyloxazoline such as its mesylate.

The hydroxymethyl compounds of Structure IV used in method B are prepared by reduction of the corresponding carboxylic acid. This reduction is typically performed by use of lithium aluminum hydride, diborane or sodium borohydride and a Lewis acid catalyst such as aluminum chloride or boron trifluoride. This carboxylic acid is prepared by reaction, preferably a base catalyzed reaction, of cysteine, preferably D-Cysteine, and the compound RX wherein R is as defined above and X is a chloro, bromo, iodo or any other good leaving group. As should be apparent, the R group must be a saturated carbon atom and will preferably be a primary carbon atom in order to facilitate the nucleophic displacement. Certain Structure I R groups are unable to undergo this requisite nucleophilic reaction, i.e., RX+Cysteine, and accordingly Structure I compounds wherein R is phenyl, furanyl, or pyridyl cannot be prepared by method B.

The Structure V amino esters of method C can be prepared from the corresponding t-butyloxycarbonyl (BOC) amine derivatives by mild acid hydrolysis. These BOC derivatives can be prepared by reaction, preferably a base catalyzed reaction of a sulfide, RSH wherein R is as defined above, with an acrylic acid of Structure VII

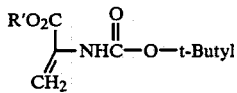

wherein R' is a 1 to 4 carbon alkyl group. Alternatively where a Structure I compound wherein R is furanyl is desired, 2,5-dimethoxy-2,5-dihydrofuran can be reacted with a 1 to 4 carbon alkyl ester of cysteine along with p-toluenesulfonic acid. Upon subsequent work up with a mild base such as sodium bicarbonate, a Structure V amino ester wherein R is furanyl is produced.

Moreover, as will be readily apparent to those skilled in the art, the use of protecting groups to prevent the formation of undesired products in the above described reactions can be desirable in many instances. For example, the phenol of N-[1-(hydroxymethyl)-2-[(4-hydroxyphenyl)thio]-ethyl]-3-[6-methyluracil]-2-propenamide is preferably silated prior to treatment with $NaIO_4$ to oxidize the thio group to a sulfinyl group.

The compounds described herein are useful antiprotozoal agents in animals. The term "animals" is intended to include inter alia mammals, such as mice, rats, guinea pigs, rabbits, ferrets, dogs, cats, cows, horses and primates including man. Also encompassed within the term animals are both fish and fowl. The term "fowl" is intended to include male or female birds of any kind including parrots and canaries, but is primarily intended to encompass poultry which are commercially raised for eggs or meat. Accordingly, the term "fowl" is particularly intended to encompass hens, cocks and drakes of chickens, turkeys and ducks.

The term "protozoa" is intended to include those members of the subphyla Sarcomastigophora and Sprozoa of the phylum Protozoa. More particularly, the term "protozoa" as used herein is intended to include those genera of parasitic protozoa which are important to man because they either cause disease in man or his domestic animals. These genera are for the most part found classified in the superclass of Mastigophora of the subphylum Sarcomastigophora and the class of Telosporea of the subphylum Sporozoa in the classification according to Baker (1969). Illustrative genera of these parasitic protozoa include Histomonas, Trypanosoma, Giardia, Trichomonas, Eimeria, Isopora, Toxoplasma and Plasmodium.

Indeed, a preferred embodiment of the present invention is the use of these compounds as antiprotozoal agents in the treatment of intestinal coccidia in commercial poultry. The economic importance of intestinal coccidia is highly significant. Thus in 1972, the estimated loss to the poultry industry in the United States due to coccidial infections was approximately 47 million dollars. Due to the rapid development of drug resistance by coccidia, and due to the relatively high toxicity of some of the drugs used in the treatment of coccidiosis, there is a need for effective coccidiostats that are non-toxic and to which intestinal coccidia do not develop rapid drug resistance.

Furthermore, the products of the present invention are antibacterial agents, having activity against Gram-positive and Gram-negative bacteria such as *Staph. aureus, E. coli, Klebsiella pneumoniae, Strep. faecalis,* and *Strep. pyogenes*.

The compounds described herein are employed in amounts that are effective against bacteria and protozoa. These amounts will depend, of course, upon various factors, such as the type and nature of the protozoal or bacterial infection, the activity of the specific compound, the age, sex and species of animal treated and whether the treatment is prophylactic or therapeutic. In general the compounds described herein can be orally or parenterally administered, preferably parenterally at a daily dose ranging from 0.1 to 100 mg/kg of patient body weight, preferably from about 1 to 50 mg/kg.

Due to the low toxicity of the compounds described herein, the compounds can be safely administered ad libitum via the drinking water of the test animals in the treatment of coccidiosis in fowl. Generally speaking, concentrations of the active ingredient ranging from about 0.1% to about 2% are suitable, depending primarily upon the nature of the protozoal infection to be treated whether prophylactic or therapeutic, the severity of the infection and the period of treatment.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula I can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The following examples illustrate the preparation of the Structure I derivatives.

EXAMPLE 1

4-[[2-phenyl-(2-oxazolin-4-yl)]methylthio]phenol

To a solution of 11.1 g (67mm) of 2-phenyl-2-oxazolin-4-yl methyl alcohol in 150 ml methylene chloride was added 5.25 ml (67 mm) of mesylchloride at 0° C. To this stirred solution under argon was added 9.4 ml (67 mm) of triethylamine over a 30 minute period. The methylene chloride was removed in vacuo. The residue was diluted with 10 ml DMF and pumped on at high vacuum. 8.5 ml (67 mm) of 4-mercaptophenol in 5 ml of DMF was added followed by 9.4 ml (67 mm) of triethyamine. After stirring for 1 day, 0.5 g sodium borohydride was added. After a total of 3 days another 0.5 g of sodium borohydride was added followed by a one hour delay. The reaction mixture was poured into 300 ml ethylacetate and washed with 3×150 ml of water, 150 ml 0.1 N, HCl, and brine, then dried over Na$_2$SO$_4$ and concentrated to a yellow oil. Dilution with 50 ml ethyl acetate and seeding gave 4.23 g of a white crystalline solid isolated by filtration mp. 114.5°–165.5° C.

EXAMPLE 2

4-[[2-Phenyl-(2-oxazolin-4-yl)]methylsulfinyl]phenol

To a solution of 2.85 q (10.0 mm) of the sulfide prepared in Example 1 in 50 ml methylenechloride at 25° C. was added 2.1 g (12 mm) of 90% MCPBA. Small portions of MCPBA were added until conversion was completed as indicated by thin layer chromatography. The soution was poured into 50 ml methylenechloride, washed with 100 ml NaHCO$_3$ solution, dried over Na$_2$SO$_4$, filtered and concentrated to give crude title compound.

EXAMPLE 3

5-benzylcysteine hydrochloride 31.5 g (200 mmole) of cysteine was dissolved in 750 ml degassed absolute ethanol. 84 ml (600 mmole) of triethylamine was added followed by 24 ml benzylbromide and the mixture was stirred at 25° C. for 18 hours. The mixture was poured into 3 l of water. The resulting transparent solution was stirred while 200 ml 1N HCl was added. Upon cooling, the crystals were filtered and suction dried to give 26.0 g (123 mmole), 62%, of a white solid, the title compound.

EXAMPLE 4

2-amino-3-benzylthio propan-1-ol

To a stirred slurry of 10.0 g of lithium aluminum hydride in 500 ml dry THF under argon was added 26.0 g (123 mmol) of 5-benzylcysteine hydrochloride carefully over a 30 minute period with cooling. The slurry was then brought to reflux for 18 hours. Upon cooling, 10.0 ml of water, 10.0 ml 15% NaOH solution and 30.0 ml of water were carefully added. Filtration, washing with ethylacetate and concentration of the filtrate gave 19.9 g of the title compound as a viscous oil.

EXAMPLE 5

Methyl 2-amino-3-[(4-hydroxyphenyl)thio]propanoatehydrochloride 20 g (100 mmol; 120 ml) methyl 2-(butoxycarbonylamino)-propenoate in chloroform was dissolved in 180 ml of methanol. 13.88 g (110 mmol) 4-mercaptophenol was added and the mixture was then stirred at room temperature under nitrogen for 24 hours. Solvents were removed in vacuo until foaming occurred, then the mixture was taken up in 700 ml dry ether. HCl gas was bubbled through the solution, quickly forming a white precipitate. Bubbling was continued for 1 hour with cooling, then the solution was cooled to 5° C. and filtered to yield the title compound in 80.8% yield.

EXAMPLE 6

Ethyl 2-Amino-3-(2-furanylthio)propanoate

To 16.25 g (125 mmol) of 2,5-dimethoxy-2,5-dihydrofuran and 23.20 g (125 mmol) of ethyl 2-amino-3-mercaptopropanoate in 100 ml dry acetonitrile was added approximately 0.15 g of tosyl chloride. The mixture was stirred 1 hour at room temperature under nitrogen during which time complete solution was attained which became very dark. The mixture was concentrated in vacuo, taken up in ethyl acetate, then extracted with aqueous NaHCO$_3$ solution followed by saturated NaCl solution. The organic portion was dried over MgSO$_4$, filtered then concentrated to 50 ml. The concentrate was then chromotographed to give 8.35 g (31.0%) of the title compound as a dark oil.

EXAMPLE 7

N-[1-Carbomethoxy-2-[(4-hydroxyphenyl)thio]ethyl]-3-(6-methyluracil)-2-propenamide.

730 mg (3.15 mmol) of amino ester from Example 5 in 5 ml of dry DMF was treated with 0.24 ml (3.15 mmol) triethylamine. The resulting precipitate was filtered and 0.61 g (3.15 mmol) 6-methyluracylacrylic acid along with 0.47 g (3.47 mmol) HOBT was added. The flask was warmed slightly to make the mixture more homogeneous, then cooled to ~ −15° C. before adding 0.65 g (3.15 mmol) of DCC. The mixture was stirred 24 hours at room temperature. Ethanol was added and the mixture filtered. DMF was removed via kugelrohr at 70° C. The remaining solid was taken up in ethanol and filtered. The filtrate was concentrated in vacuo then diluted with ethanol, cooled to −15° C. then filtered. All portions were combined, concentrated then chromatographed on silica to give the title compound.

EXAMPLE 8

N-[1-(hydroxymethyl)-2-(benzylthio)ethyl]-3-(6-methyluracil)-2-propenamide 9.9 g (50 mmol) of the amine from example 4 and 10.0 g (50 mmol) of 6-methyluracylacrylic acid were dissolved in 125 ml degassed DMF. The stirred solution was cooled to 0° C. and 9.0 g of 1-hydroxybenztriazole and 11.5 g of DCC were added (56 mmol). The reaction was allowed to proceed for 3 days at room temperature, then filtered and was washed with ethylacetate. The combined filtrate was diluted with 1L ethylacetate, washed with dilute HCl, saturated NaHCO$_3$ solution, and then brine. Drying over Na$_2$SO$_4$ and concentration in vacuo gave 10.6 g of the title compound as a tan solid.

EXAMPLE 9

4-[(3-benzoyloxy-2-aminopropyl)sulfinyl]phenol hydrochloride 1.3 g (4.3 mM) of the oxazoline from Example 2 was dissolved in 30 mL ethanol and treated with 8 mL 1N HCl for 3 hours. The solvents were removed under reduced pressure and the resulting foam was dried under high vacuum for 18 hours at 50° C. to give the title compound.

EXAMPLE 10

N-[1-(Benzoyloxymethyl)-2-[[4-(hydroxy)phenyl]sulfinyl]-ethyl]-3-(6-methyluracil)-2-propanamide The HCl salt from Example 9 was dissolved in 15 ml of dry DMF and treated at 25° C. with 900 mg (4.5 mm) of 6-methyluracilacrylic acid, 1.0 g of HOBT, 600 μL (0.43 mm) of triethylamine and 1.2 g of DCC. The resulting mixture was stirred for 3 days, then treated with 10 drops of H$_2$O, stirred for 1 hour, filtered, and the DMF was removed under high vacuum (50° C. at 0.1 mm). The residue was taken up in dimethylsulfoxide and chromatographed on silica gel to give the title compound as a tan solid.

EXAMPLE 11

N-[1-(Hydroxymethyl)-2-[[4-(hydroxy)phenyl]sulfinyl]-ethyl]-3-(6-methyluracil)-2-propenamide To a mixture of 1500 mg (3.0 μM) of benzoate from Example 10 in 30 ml of ethanol at 25° C. was added 15 ml of 1N LiOH. After 1 hour, 2.5 ml of 6N HCl was added and the solvents were removed in vacuo. The solid was dissolved in 5 ml of H$_2$O and 10 ml of ethanol, then heated and allowed to cool. The solid was filtered, washed with H$_2$O, and dried under high vacuum to give 640 mg of the title compound as an off white powder.

EXAMPLE 12

N-[1-(Hydroxymethyl)-2-[(phenylmethyl)sulfinyl]ethyl]-3-(6-methyluracil)-2-propenamide 4.7 g (11.6 mmol) of sulfide from Example 8 was dissolved in 90 ml of dioxane and 45 ml of H$_2$O, then treated with 3.0 g (14.0 mmol) of powdered NaIO$_4$. After stirring at 25° C. for 18 hours, the mixture was diluted with 250 ml of isopropanol and filtered. The filtrate was concentrated to an oily residue, which upon chromatography yielded the title compound.

EXAMPLE 13

N-[1-(Hydroxymethyl)-2-[[4-(hydroxy)phenyl]sulfinyl]-ethyl]-3-[6-(methyl)uracil]-2-propenamide 2.0 g (4.94 mmol) of the sulfide from Example 7 and 0.84 g (12.4 mmol) of imidazole were dissolved in 25 ml DMF. 1.11 g (7.41 mmol) of t-butyldimethylsilylchloride was then added and the mixture stirred 20 hours at room temperature. The mixture was filtered and DMF removed via rotary evaporation at high vacuum. The residue was taken up in 10 ml of 20% MeOH/EtOAC and chromatographed using 0 →10% MeOH/EtOAC to give the 0- silated product.

To 0.145 g (6.58 mmol) of LiBH$_4$ in 30 ml dry DMF was added 1.14 g (2.19 mmol) of the silyl derivative. 0.0228 g (0.22 mmol) of trimethoxyborane was then added and the mixture stirred at room temperature for 20 hours. 100 mg (4.55 mmol) of LiBH$_4$ was then added and the mixture stirred an additional 44 hours. Subsequently, 20 ml of H$_2$O was added followed by 1N HCl added until the light yellow reaction mixture became colorless. The solution was poured into 100 ml of ethyl acetate and any remaining precipatate was dissolved in 1N HCl and poured into the ethylacetate solution. The aqueous portions were extracted 3 times with 100 ml of ethyl acetate, then washed with brine followed by drying over MgSO$_4$. The mixture was filtered followed by concentration to dryness in vacuo to give 1.02 g (94.7% of the hydroxymethyl-0-silylated sulfide product at a white powder.

1.00 g (2.03 mmol) of this sulfide was dissolved in 50 ml of methanol, then 25 ml of H$_2$O and 0.435 g (2.03 mmol) of NaIO$_4$ was added. This mixture was stirred at room temperature for 16 hours then poured into 50 ml of isopropanol and filtered to give a solid product. Upon subsequent chromatography the 0-silated sulfinyl derivative was isolated in 49% yield.

Finally 28 mg of this white powder was treated in refluxing acetonitrile with excess CsF. Solvent was removed in vacuo and the material chromatographed on silica using 5% H$_2$O/ acetone to give the title compound in 79% yield.

We claim:

1. A method of inhibiting the growth of protozoa in animals in need thereof which comprises administering an antiprotozoal amount of a compound of the formula

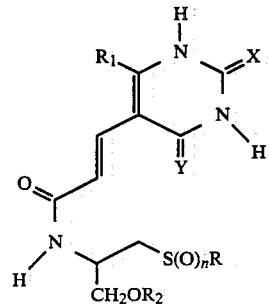

wherein X and Y are each independently an oxo or an imino group; n is 0 or the integer 1 or 2; R$_1$ is a hydrogen or a 1 to 4 carbon alkyl group; R$_2$ is a hydrogen, a 1 to 4 carbon alkyl, a 2 to 5 carbon acyl or a benzoyl group; and R is a 1 to 6 carbon alkyl, 3 to 8 carbon alkenyl, pyridyl, furanyl or furfuryl group; or R is a phenyl or benzyl group each optionally substituted by a methylenedioxy group or one or two halogen, 1 to 4 carbon alkyl, 1 to 4 carbon alkoxy, 1 to 4 carbon alkylthio, hydroxy, nitro or cyano groups, or a pharmaceutically acceptable acid addition salt thereof.

2. A method of claim 1 wherein X and Y are each an oxo group.

3. A method of claim 2 wherein R is a phenyl or benzyl group each optionally substituted by a methylenedioxy group or one or two halogen, 1 to 4 carbon alkyl, 1 to 4 carbon alkoxy, 1 to 4 carbon alkylthio, hydroxy, nitro or cyano groups.

4. A method of claim 3 wherein the phenyl or benzyl group is substituted at the para position.

5. A method of claim 3 wherein R is a pyridyl, furanyl or furfuryl group.

6. A method of claim 2 wherein $R_1$ is a methyl group and $R_2$ is a hydrogen group.

7. A method of claim 2 wherein R is a 3 to 8 carbon alkenyl group.

8. A method of claim 2 wherein n is the integer 1.

* * * * *